(12) United States Patent
Lam et al.

(10) Patent No.: US 10,179,227 B2
(45) Date of Patent: Jan. 15, 2019

(54) RESILIENT TUBE OVER DILATOR BALLOON

(71) Applicant: Acclarent, Inc., Menlo Park, CA (US)

(72) Inventors: Sivette Lam, Milpitas, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 1209 days.

(21) Appl. No.: 13/795,999

(22) Filed: Mar. 12, 2013

(65) Prior Publication Data
US 2014/0277061 A1    Sep. 18, 2014

(51) Int. Cl.
*A61M 25/10* (2013.01)
*A61M 29/02* (2006.01)

(52) U.S. Cl.
CPC .......... *A61M 29/02* (2013.01); *A61M 25/104* (2013.01); *A61M 2025/1081* (2013.01); *A61M 2025/1084* (2013.01); *A61M 2210/1028* (2013.01); *A61M 2210/1032* (2013.01); *A61M 2210/1035* (2013.01)

(58) Field of Classification Search
CPC ................ A61M 29/02; A61M 25/104; A61M 2025/1013; A61M 2025/1015; A61M 25/1011; A61M 2025/1075; A61M 2025/1077; A61M 2025/1081; A61M 2025/1084; A61M 25/10; A61M 25/1018; A61M 25/10184; A61M 25/1038
See application file for complete search history.

(56) References Cited

U.S. PATENT DOCUMENTS

| | | | | |
|---|---|---|---|---|
| 4,771,776 A | * | 9/1988 | Powell | A61M 25/1002 604/103.05 |
| 5,116,318 A | * | 5/1992 | Hillstead | A61F 2/90 604/103.05 |
| 5,257,974 A | * | 11/1993 | Cox | A61M 25/104 600/585 |
| 5,338,300 A | * | 8/1994 | Cox | A61M 25/104 604/103.05 |
| 5,545,209 A | * | 8/1996 | Roberts | A61F 2/958 604/103.05 |
| 5,628,755 A | * | 5/1997 | Heller | A61F 2/958 604/96.01 |

(Continued)

FOREIGN PATENT DOCUMENTS

| | | |
|---|---|---|
| EP | 0 553 960 A1 | 8/1993 |
| EP | 0 897 730 A2 | 2/1999 |

(Continued)

OTHER PUBLICATIONS

U.S. Appl. No. 13/796,073, filed Mar. 12, 2013.
International Search Report and Written Opinion dated Jun. 26, 2014 for Application No. PCT/US2014/018042, 11 pgs.

*Primary Examiner* — Ryan J Severson
(74) *Attorney, Agent, or Firm* — Frost Brown Todd LLC

(57) ABSTRACT

A dilation device comprises an elongate shaft, an inflatable balloon, and a resilient tube. The inflatable balloon is disposed along the shaft. The resilient tube is also disposed along the shaft and is positioned to encompass at least part of the inflatable balloon. The resilient tube is configured to impose an inwardly directed resilient bias on at least a portion of the exterior of the inflatable balloon. At least part of the resilient tube is secured to one or both of the elongate shaft or the inflatable balloon.

20 Claims, 6 Drawing Sheets

(56) References Cited

U.S. PATENT DOCUMENTS

| | | | | |
|---|---|---|---|---|
| 5,843,027 | A * | 12/1998 | Stone | A61F 2/958 |
| | | | | 604/509 |
| 5,908,448 | A * | 6/1999 | Roberts | A61F 2/958 |
| | | | | 606/194 |
| 6,068,634 | A * | 5/2000 | Lorentzen Cornelius | A61F 2/958 |
| | | | | 606/198 |
| 6,296,660 | B1 * | 10/2001 | Roberts | A61F 2/958 |
| | | | | 623/1.11 |
| 6,506,202 | B1 * | 1/2003 | Dutta | A61F 2/958 |
| | | | | 604/103.05 |
| 6,537,247 | B2 * | 3/2003 | Shannon | A61M 25/104 |
| | | | | 604/103.05 |
| 6,695,863 | B1 * | 2/2004 | Ramzipoor | A61M 25/104 |
| | | | | 604/103.05 |
| 6,830,575 | B2 * | 12/2004 | Stenzel | A61F 2/95 |
| | | | | 606/108 |
| 6,872,223 | B2 * | 3/2005 | Roberts | A61F 2/958 |
| | | | | 623/1.11 |
| 7,727,191 | B2 * | 6/2010 | Mihalik | A61B 18/02 |
| | | | | 604/101.01 |
| 7,815,649 | B2 * | 10/2010 | Layne | A61B 17/3417 |
| | | | | 606/105 |
| 8,211,055 | B2 * | 7/2012 | Christiansen | A61M 25/10 |
| | | | | 604/101.02 |
| 8,444,686 | B2 * | 5/2013 | Holman | A61F 2/0095 |
| | | | | 623/1.11 |
| 8,709,034 | B2 * | 4/2014 | Keast | A61B 17/221 |
| | | | | 606/185 |
| 9,095,364 | B2 * | 8/2015 | Muni | A61M 16/04 |
| 9,278,202 | B2 * | 3/2016 | Ranade | A61M 29/02 |
| 9,370,643 | B2 * | 6/2016 | Hedberg | A61M 25/104 |
| 9,913,964 | B2 * | 3/2018 | Muni | A61M 25/0152 |
| 2005/0090852 | A1 * | 4/2005 | Layne | A61B 17/3417 |
| | | | | 606/190 |
| 2005/0137620 | A1 * | 6/2005 | Alkhatib | A61B 17/22031 |
| | | | | 606/194 |
| 2006/0270982 | A1 * | 11/2006 | Mihalik | A61B 18/02 |
| | | | | 604/113 |
| 2008/0140003 | A1 * | 6/2008 | Bei | A61F 2/95 |
| | | | | 604/103.05 |
| 2010/0069839 | A1 * | 3/2010 | Holman | A61F 2/0095 |
| | | | | 604/103.05 |
| 2010/0168511 | A1 | 7/2010 | Muni et al. | |
| 2011/0060275 | A1 * | 3/2011 | Christiansen | A61M 25/10 |
| | | | | 604/101.02 |
| 2012/0289776 | A1 * | 11/2012 | Keast | A61B 17/221 |
| | | | | 600/106 |
| 2012/0330232 | A1 * | 12/2012 | Hedberg | A61M 25/104 |
| | | | | 604/103.05 |
| 2013/0090624 | A1 * | 4/2013 | Munsinger | A61F 2/958 |
| | | | | 604/500 |
| 2013/0253466 | A1 * | 9/2013 | Campbell | A61M 25/10 |
| | | | | 604/500 |
| 2014/0066897 | A1 * | 3/2014 | Campbell | A61L 29/041 |
| | | | | 604/509 |
| 2014/0277061 | A1 * | 9/2014 | Lam | A61M 29/02 |
| | | | | 606/192 |

FOREIGN PATENT DOCUMENTS

| | | |
|---|---|---|
| WO | WO 95/08965 A1 | 4/1995 |
| WO | WO 2010/144483 A1 | 12/2010 |

* cited by examiner

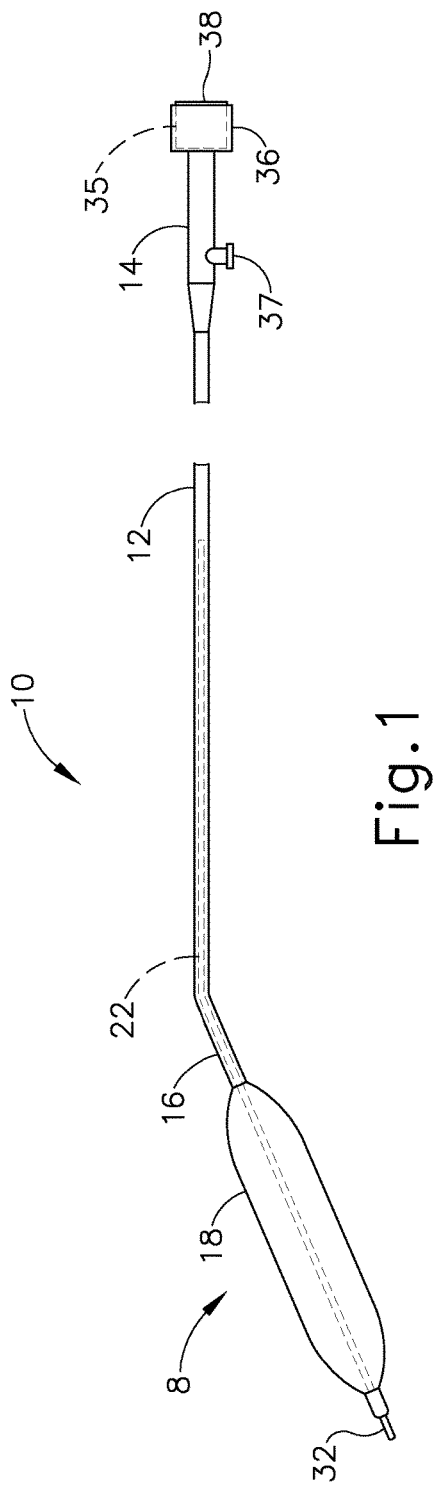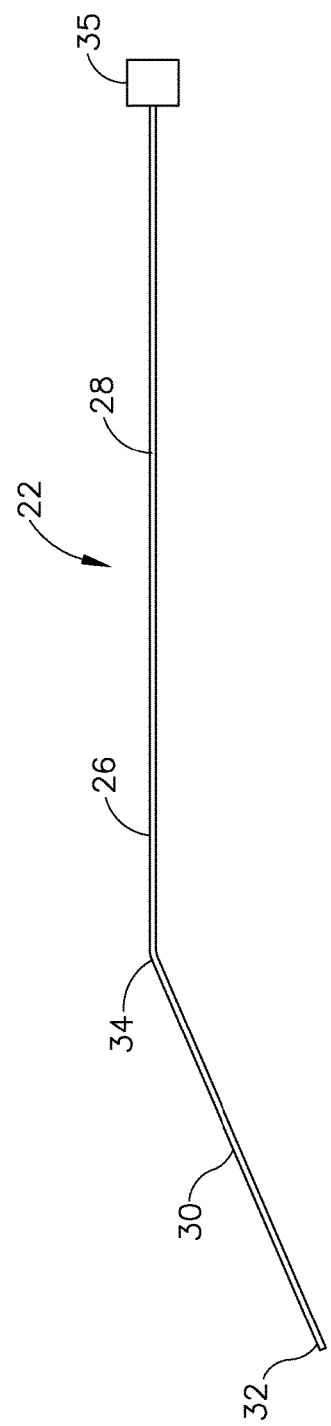

RESILIENT TUBE OVER DILATOR BALLOON

BACKGROUND

In some instances, it may be desirable to dilate an anatomical passageway in a patient. This may include dilation of ostia of paranasal sinuses, dilation of a patient's airway (e.g., to treat a stenosis within the larynx), dilation of the nasal cavity, dilation of the Eustachian tube, dilation of other passageways within the ear, nose, or throat, dilation of blood vessels, dilation of the urethra, etc. One method of dilating anatomical passageways includes using a guide wire and catheter to position an inflatable balloon within the anatomical passageway, then inflating the balloon with a fluid (e.g., saline) to dilate the anatomical passageway.

Airway stenosis (or "airway narrowing") is a medical condition that occurs when some portion of a patient's airway becomes narrowed or constricted, thus making breathing difficult. A stenosis may occur in any part of the airway including the larynx, trachea, bronchi, or a combination of any of the above mentioned regions. Both adults and children may develop a stenosis. In some instances, a stenosis is caused by intubation, which is when a tube is placed in the airway for ventilation/breathing assistance in a patent who cannot breathe. Intubation for prolonged periods of time may traumatize the airway, causing scar tissue formation that forms the stenosis.

Therapies for treating an airway stenosis range from endoscopic treatments, such as dilation and laser resection, to open procedures, such as laryngotracheal reconstruction. In one technique, a series of rigid dilators of increasing diameter are pushed down the airway, gradually expanding the constriction but also applying shear forces to the airway. Balloon catheters may also be used to perform dilation of an airway or other anatomical passageway. For instance, the expandable balloon may be positioned within a stenosis in an airway (e.g., larynx, trachea, bronchi, etc.) and then be inflated, to thereby dilate the airway and increase airflow. The dilated airway may then allow for improved breathing. Once the balloon is deflated or subjected to negative pressure, however, the balloon may tend to lose its shape and become flat, folded, or otherwise non-cylindraceous. An example of a system that may be used to perform dilation procedures is described in U.S. Pub. No. 2010/0168511, entitled "System and Method for Dilating an Airway Stenosis," published Jul. 1, 2010, now U.S. Pat. No. 9,913,964, issued Mar. 13, 2018, the disclosure of which is incorporated by reference herein.

While several airway dilation systems have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side view of an exemplary system for dilating a stenosis in the airway, including a balloon catheter and a stylet;

FIG. 2 depicts a side view of the stylet of FIG. 1;

Figure 3A:
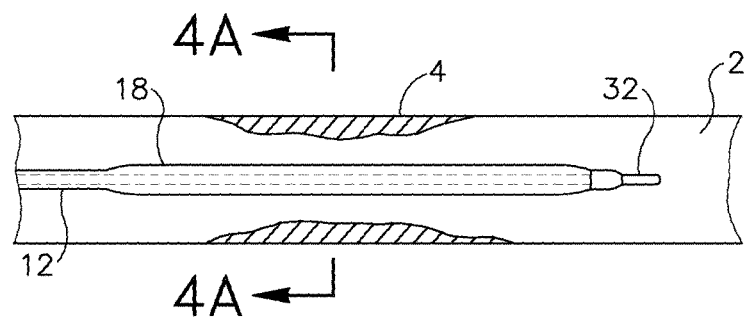
FIG. 3A depicts a detailed side elevation view of the inflatable balloon of FIG. 1, within a stenotic region of an airway within a patient.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Balloon Dilation Catheter System

FIG. 1 shows an exemplary dilation catheter system (8), which may be used to dilate a stenosis in an airway; or to dilate some other anatomical passageway (e.g., within the ear, nose, throat, cardiovascular system, etc.). At least part of system (8) may be constructed and operable in accordance with at least some of the teachings of U.S. Pub. No. 2010/0168511, now U.S. Pat. No. 9,913,964, issued Mar. 13, 2018, the disclosure of which is incorporated by reference herein. It should be understood that dilation catheter system (8) may be used to dilate either a naturally occurring passageway in a patient or a surgically created passageway in a patient.

Dilation catheter system (8) of this example comprises a balloon catheter (10) and a stylet (22). Balloon catheter (10) comprises a shaft (12) positioned between a hub (14) and a balloon (18). Balloon (18) is coupled to a distal end of shaft (12) and is configured to receive fluid through balloon catheter (10). Stylet (22) is slidably positioned through balloon catheter (10). In some versions, at least a portion of stylet (22) has a greater stiffness than at least a portion of balloon catheter (10), such that when stylet (22) is bent and inserted within balloon catheter (10), balloon catheter (10) at least partially conforms to the shape of stylet (22). In a dilation procedure, stylet (22) is used to advance balloon catheter (10) within an airway or targeted anatomical passageway (e.g., at a stenosis site). Balloon (18) may then be actuated to an expanded state to open or dilate the targeted anatomical passageway. Balloon (18) may then be actuated back to a collapsed state such that balloon (18) is deflated. This process may be repeated to dilate several anatomical passageways.

A. Exemplary Balloon Catheter

As shown in FIG. 1, balloon catheter (10) comprises a catheter shaft (12). An inflatable balloon (18) is attached to a distal end of shaft (12) via adhesive or other attachment means. A hub (14) is coupled to a proximal end of shaft (12) and comprises a stylet port (38) and an inflation port (37). Stylet (22) is inserted within stylet port (38) and generally resides within an inner lumen of shaft (12). Fluid (e.g., saline, etc.) is introduced through inflation port (37) through shaft (12) to inflate balloon (18).

Balloon catheter (10) may have any number of suitable sizes, shapes and configurations. For example, balloon (18) may have different lengths and diameters in different embodiments, to accommodate different patient anatomies. The overall catheter (10) length and diameter may also vary. For example, the overall length of balloon catheter (10) (i.e., from the proximal end of hub (14) to the distal end of catheter shaft (12)) is about 35-70 cm, such as less than or equal to about 50 cm, or about 45 cm.+−.5 cm. Catheter (10) may be handled and manipulated with one hand. The working length of balloon (18) in FIG. 1 is about 40 mm+/−0.2 mm. By "working length" it is meant the length between the two tapered portions of balloon (18). In some versions, the working length of balloon (18) may range from between about 10 mm and about 60 mm such as about 16-45 mm. The outer diameter of the fully inflated working length of balloon (18) may also vary. In the present example, balloon (18) has an inflated diameter of about 14.1 mm+/−0.5 mm. In some versions, balloon (18) diameter may range from about 3 mm to about 24 mm, such as about 5-15 mm. A combination of balloon diameters and lengths may be provided, such that a physician may choose an appropriate size for an adult or pediatric patient. In one example, the following balloon diameters and lengths may be provided: 5 mm by 24 mm; 7 mm by 24 mm; 10 mm by 40 mm; and 14 mm by 40 mm. Of course, any of a number of other combinations of sizes of balloons (58) may be provided.

Any suitable material may be used to form balloon (18). Balloon (18) may be compliant, semi-compliant or non-compliant. Balloon (18) may be made of nylon, some other polymer, such as PTFE, and/or any other suitable material (s). In some versions, balloon (18) is formed of an elastic/extensible material that is resiliently biased to assume a shrunken, non-inflated configuration, such that the material forming balloon (18) is under increased tension when balloon (18) is in a non-deflated state. In some other versions, balloon (18) is formed of a material that is flexible yet substantially inelastic/non-extensible, such that the material forming balloon does not provide a significant resilient bias. In other words, balloon (18) does not stretch in response to increased fluid pressure inside balloon (18), even though the effective outer diameter of balloon (18) increases in response to increased fluid pressure. Such inelastic versions of balloon (18) may nevertheless be filled with fluid, with the fluid pressure being increased to provide an outwardly directed force via balloon (18), and this process may be referred to as "inflating." When the pressure of fluid inside balloon (18) is reduced, this process may be referred to as "deflating," even if the material forming balloon (18) does not elastically shrink, since balloon (18) may nevertheless flexibly collapse in response to reduced fluid pressure. Thus, it should be understood that the use of terms like "inflate," "inflated," "deflate," and "deflated" does not necessarily mean that the material forming balloon (18) undergoes any elastic stretching or shrinking as the fluid pressure within balloon (18) changes.

In some versions, balloon (18) may include an outer slip-resistant surface, which may be formed by a textured surface or a coating. Such a surface may help prevent slipping of balloon (18) out of an airway structure during inflation and/or may facilitate re-wrapping balloon (18) by hand after deflation if balloon (18) is to be used for a second or subsequent dilation procedure. Examples of such balloons are provided in U.S. Patent Pub. No. 2014/0277071, now abandoned, entitled "Features to Enhance Grip of Balloon within Airway," filed on a date even herewith, the disclosure of which is incorporated by reference herein.

Catheter shaft (12) may also be formed of any suitable material. It may be desirable to form shaft (12) from material(s) selected so that shaft (12) is unlikely to kink when bent, such as when bent by stylet (22) and/or a user. One such material, for example, is Pebax, although other polymers may be used. Shaft (12) may also have any suitable color and may include one or more shaft markings. The shaft color and markings may be built into shaft (12) by using a colored material or may be added by applying paint or another colorant. In some versions, shaft (12) may have a dark color, such as black or dark blue, and one or more light colored markings may be applied over the dark shaft (12). In some versions, the markings (not shown) may include direct visualization markings (viewed directly with the naked eye or an endoscope) and/or radiographic markings (viewed with a radiographic device such as intraoperative fluoroscopy). Any suitable combination, size and color of markings may be used. One example of shaft color and shaft markings, which could be used or modified for a balloon catheter, is the Relieva Solo Pro™ Sinus Balloon Catheter, manufactured by Acclarent, Inc. of Menlo Park, Calif.

B. Exemplary Stylet

FIG. 2 shows stylet (22) in greater detail. Stylet (22) comprises a core member (26) with a proximal section (28) and a distal section (30). A coil (32) is disposed around at least part of distal section (30) of core member (26). A luer lock member (35) is coupled with a proximal end of core member (26) for coupling with a hub on balloon catheter (10). In some versions, stylet (22) does not include a coil (32). Core member (26) and/or coil (32) may be formed of nitinol, stainless steel, or other biocompatible materials. Distal portion (30) of stylet (22) includes a bend or curve (34) that is stiff enough to bend balloon catheter (10) during the placement of balloon catheter (10) within the airway of the patient. In some versions, stylet (22) may be provided in a generally straight configuration. Stylet (22) may be preformed to have a bend (34), or stylet (22) may be malleable, such that a user may bend stylet (22) and stylet (22) maintains the user-created bend. This malleability allows a user to adjust a bend angle according to the airway anatomy of a particular patient. Proximal section (28) of stylet (22) may be generally stiff, a distal section (30) may be generally malleable, and an extreme distal portion may be atraumatic and very flexible or even floppy. This variation in flexibility along the length of stylet (22) may be achieved by using different materials, such as stainless steel and nitinol. Alternatively, one material, such as stainless steel, may be used and the diameter of stylet (22) may be altered to achieve the variation in flexibility along the length of stylet (22).

Stylet (22) has an overall length approximately as long or slightly longer than balloon catheter (10). In some versions, stylet (22) includes an atraumatic, flexible distal tip portion that extends distally out of balloon catheter (10) when stylet (22) is fully disposed within catheter (10). This tip portion may be, for example, between about 0.25 cm to about 8 cm (e.g., about 1-5 cm) in length; and may facilitate the ability of a user to advance system (8) through a patient's airway atraumatically. The overall length of stylet (22) may vary from about 30 cm to about 80 cm, such as from about 45 cm to about 60 cm. Of the overall length, a flexible distal portion of stylet (22) may be from about 5-20 cm, such as from about 10-15 cm. Bend (34) may have any suitable angle, such as from greater than 0 degrees to about 20 degrees. The diameter of stylet (22) may be less than about 1.3 mm, such as 0.9 mm or less. The diameter may decrease distally to about 0.13 mm+/−0.013 mm. Of course, the foregoing dimensions are mere examples. Any other suitable dimensions may be used.

Stylet (22) may be attached to balloon catheter (10), or stylet (22) may be removably connected to balloon catheter (10). Stylet (22) comprises a luer lock member (35) with threads on proximal section (28) that screw into opposing threads disposed on a luer (36) of balloon catheter (10). In some versions, balloon catheter (10) may include a locking mechanism (not shown) to lock stylet (22) in position within catheter (10). The locking mechanism can be any mechanical device, including a lever, a ball and pin, a luer, etc. All or part of distal section (30) of stylet (22) may extend out of the distal end of catheter (10). Stylet (22) may be locked to balloon catheter (10) at different positions or lengths so the distal end of stylet (22) extends out of or is positioned within balloon catheter (10) at different lengths. The length, diameter(s) and stiffness characteristics of stylet (22) may be varied in different embodiments to confer different performance characteristics to the overall system (8).

Use of stylet (22) to insert balloon catheter (10) helps to guide the distal end of balloon catheter (10) through the airway of the patient and to the stenotic region. Stylet (22) provides increased steerability during advancement of balloon catheter (10). Torquability of balloon catheter (10) is also increased when using stylet (22). In some versions, luer lock member (35) of stylet (22) and luer (36) of balloon catheter (10) mate together, so that stylet (22) and balloon catheter (10) may be rotated together and thus steered into a constricted portion of an airway.

In some versions, stylet (22) may have a light emitting portion, such as a light emitting distal end or tip. For example, stylet (22) may include one or more light fibers to transmit light from a light source attached to the proximal end of stylet (22) to its distal end. Light from a light emitting stylet (22) may be used to help a user visualize a patient's airway from the inside using a scope and/or in some cases from the outside via transillumination through the patient's skin. A light emitting guidewire device that may be used or modified to achieve such an illuminating stylet (22) is the Relieva Luma™ Sinus Illumination Guidewire/System, manufactured by Acclarent, Inc. of Menlo Park, Calif. Such an illuminating stylet (22) may have any of the features described above with the additional feature of light emitting capability.

C. Exemplary Method of Use of the System

Figure 3B:
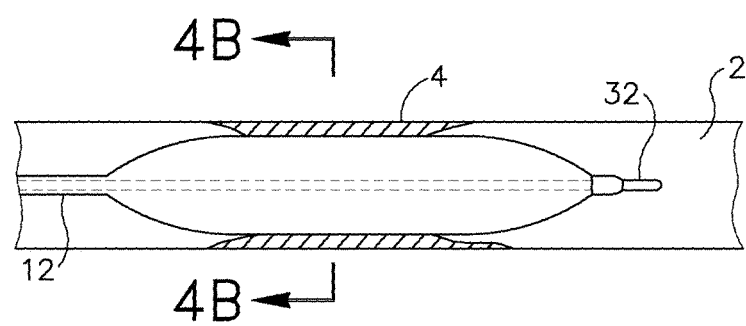
FIG. 3B depicts a detailed side elevation view of the inflatable balloon of FIG. 1, inflated to dilate a stenosis within the airway.
Figure 3C:
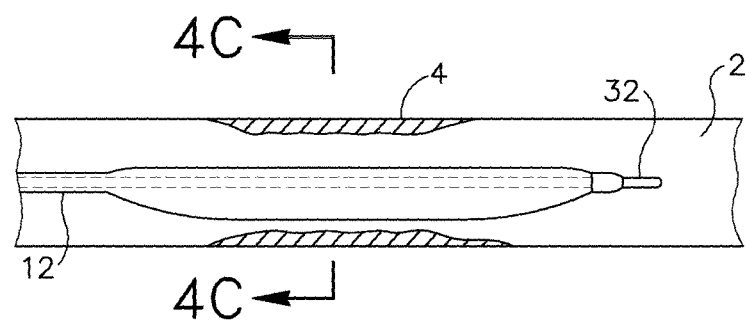
FIG. 3C depicts a detailed side elevation view of the inflatable balloon of FIG. 1, deflated within a now dilated region of the airway.
Figure 4A:
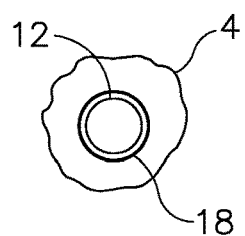
FIG. 4A depicts a cross sectional view of the inflatable balloon of FIG. 1, taken along line 4A-4A of FIG. 3A.
Figure 4B:
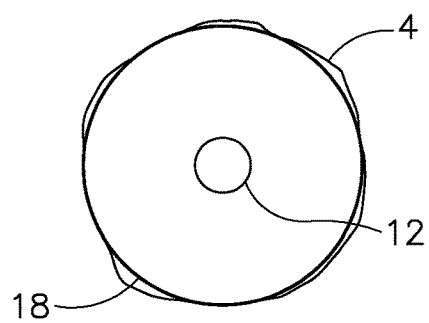
FIG. 4B depicts a cross sectional view of the inflatable balloon of FIG. 1, taken along line 4B-4B of FIG. 3B.
Figure 4C:
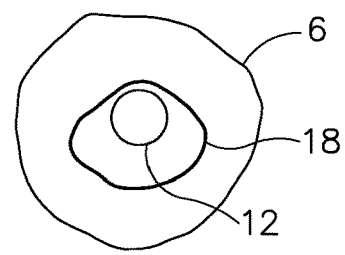
FIG. 4C depicts a cross sectional view of the inflatable balloon of FIG. 1, taken along line 4C-4C of FIG. 3C.

FIGS. 3A-3C and 4A-4C show a method for dilating an stenotic region (4) in an airway (2), such as in a case of subglottic stenosis. Dilation system (8) is introduced through the mouth and into the airway of the patient. Optionally, a bronchoscope (not shown) or other scope device may be used to visualize the positioning of dilation system (8). Dilation system (8) may be bent either by the user or by the manufacturer of system (8). For example, stylet (22) may be bent and then inserted into balloon catheter (10), while in other cases stylet (22) and balloon catheter (10) may be bent together, with stylet (22) already residing in catheter (10). The support of stylet (22) and the bend in the overall system (8) may help a physician navigate system (8) through the patient's airway to position balloon (18) within at least a portion of stenotic region (4). As shown in FIGS. 3A and 4A, inflatable balloon (18) of the catheter (10) is in an unexpanded configuration during advancement and placement of balloon catheter (10). As shown in FIGS. 3B and 4B, once balloon (18) is positioned within stenotic region (4) of the airway (2), inflatable balloon (18) is inflated to dilate stenotic region (4). Balloon (18) is then deflated to enable removal from airway (2). By way of example only, balloon (18) may be deflated by actively drawing the fluid from balloon (18); by venting the fluid in balloon (18), allowing the inward pressure imposed by airway (2) to drive fluid from balloon (18); or in any other suitable fashion as will be apparent to those of ordinary skill in the art in view of the teachings herein. As can be seen in FIGS. 3C and 4C, inflatable balloon (18) loses its initial shape and becomes misshapen and flat after balloon (18) is deflated. In some instances, this flat deflated configuration may make it difficult to remove balloon (18) from airway (2) without causing trauma on the tissue of airway (2).

In some versions, stylet (22) remains in balloon catheter (10) during inflation of balloon (18). Maintaining stylet (22) in catheter (10) during inflation may give catheter (10) added column strength and help maintain the position of balloon (18) within stenotic region (4), thus avoiding slipping. In some versions, stylet (22) is removed from balloon catheter (10) before inflating. Stylet (22) may be removed from balloon catheter (10) after balloon catheter (10) is properly positioned within airway (2) of the patient, or stylet (22) can be removed after stenosis (4) has been dilated but before removing balloon catheter (10) from the patient.

Inflatable balloon (18) may be inflated more than once to dilate stenotic region (4) of airway (2). The physician inflates inflatable balloon (18) to a desired pressure during each dilation of stenosis (4). Proper dilation of stenotic region (4) can be confirmed by visualizing the region with the bronchoscope/endoscope.

II. Exemplary Variation of Inflatable Balloon with Resilient Outer Tube

FIGS. 5A-6C show a version of inflatable balloon (18) with a resilient tube (50) disposed about the exterior of balloon (18). It should be understood that a balloon (18) with resilient tube (50) may be readily incorporated into system (8) as described above. It may be desirable to utilize a resilient tube (50) encompassing inflatable balloon (14) to prevent loss of shape and flattening of inflatable balloon (14) after inflatable balloon (14) has been inflated and deflated multiple times or subjected to negative pressure. Such a resilient tube (50) may be made of silicone, rubber, or any other resilient material; and may be capable of stretching outwardly, longitudinally, vertically, horizontally, etc. The material forming resilient tube (50) may provide increased friction within airway (2), thereby reducing the risk of inflated balloon (18) slipping within stenotic region (4) or elsewhere within airway (2). In the present example, resilient tube (50) is resiliently biased to assume a reduced diameter configuration, such as the configuration shown in FIGS. 5A, 5C, 6A, and 6C. Thus, resilient tube (50) imposes an inwardly directed resilient bias on the exterior of inflatable balloon (18), whether inflatable balloon (18) is inflated or deflated.

By way of example only, resilient tube (50) may have a length of approximately 3 inches, an inner diameter between approximately 0.125 inches and approximately 0.135 inches, and a wall thickness between approximately 0.025 inches and approximately 0.030 inches. Alternatively, any other suitable dimensions may be used.

Figure 7:
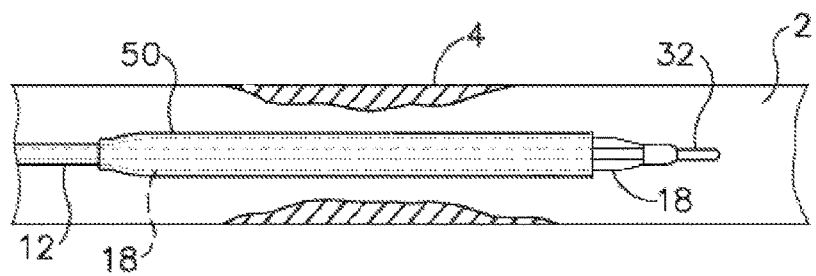
FIG. 7 depicts a detailed side elevation view of an exemplary alternative inflatable balloon with a resilient tube cover, within a stenotic region of an airway within a patient.

In the present example, the proximal end of resilient tube (50) is proximal to the proximal end of balloon (18); and the distal end of resilient tube (50) is distal to the distal end of balloon (18). Thus, resilient tube (50) fully encompasses balloon (18). In some other versions, resilient tube (50) only partially encompasses balloon (18). For instance, in some versions the proximal end of resilient tube (50) is proximal to the proximal end of balloon (18); and the distal end of resilient tube (50) is proximal to the distal end of balloon (18), as shown in FIG. 7. As yet another merely illustrative variation, the proximal end of resilient tube (50) may be distal to the proximal end of balloon (18); while the distal end of resilient tube (50) is distal to the distal end of balloon (18). Alternatively, any other suitable relationship may be used.

In the present example, the proximal end of resilient tube (50) is proximal to the proximal end of balloon (18); and the distal end of resilient tube (50) is distal to the distal end of balloon (18). Thus, resilient tube (50) fully encompasses balloon (18). In some other versions, resilient tube (50) only partially encompasses balloon (18). For instance, in some versions the proximal end of resilient tube (50) is proximal to the proximal end of balloon (18); and the distal end of resilient tube (50) is proximal to the distal end of balloon (18). As yet another merely illustrative variation, the proximal end of resilient tube (50) may be distal to the proximal end of balloon (18); while the distal end of resilient tube (50) is distal to the distal end of balloon (18). Alternatively, any other suitable relationship may be used.

Figure 5A:
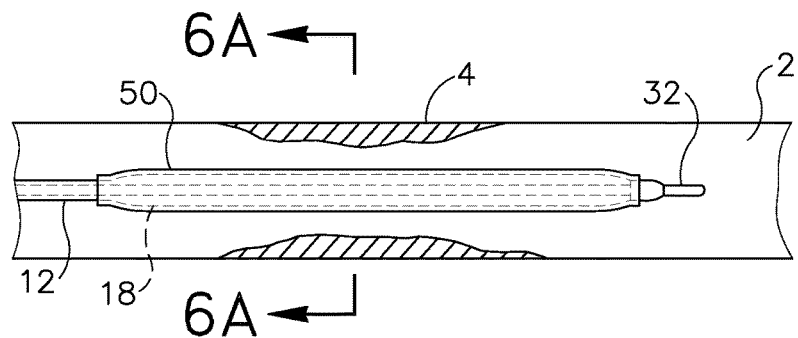
FIG. 5A depicts a detailed side elevation view of an exemplary alternative inflatable balloon with a resilient tube cover, within a stenotic region of an airway within a patient.
Figure 5B:
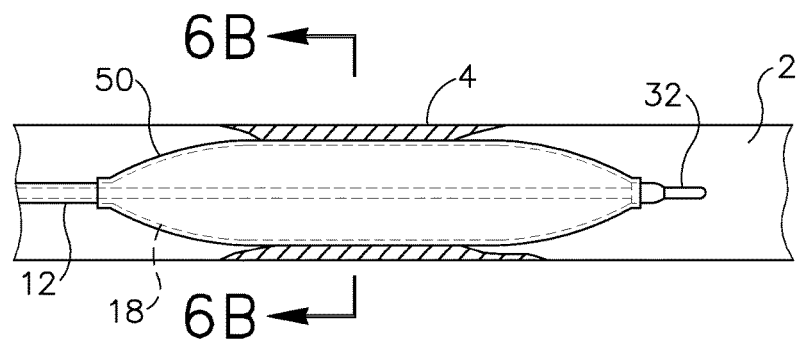
FIG. 5B depicts a detailed side elevation view of the inflatable balloon of FIG. 5A, inflated to dilate a stenosis within the airway.
Figure 6A:
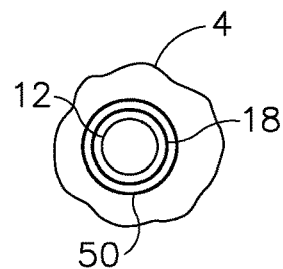
FIG. 6A depicts a cross sectional view of the inflatable balloon of FIG. 5A, taken along line 6A-6A of FIG. 5A.
Figure 6B:
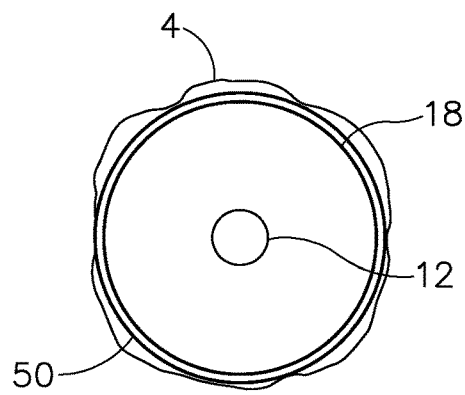
FIG. 6B depicts a cross sectional view of the inflatable balloon of FIG. 5A, taken along line 6B-6B of FIG. 5B.

As shown in FIGS. 5A and 6A, inflatable balloon (18) and resilient tube (50) are advanced through airway (2) of the patient to position inflatable balloon (148 and resilient tube (50) within at least a portion of a stenotic region (4). Saline is then communicated to balloon (18) to inflate balloon (18), as shown in FIGS. 5B and 6B. Inflation of inflatable balloon (18) expands resilient tube (50) and dilates the stenotic region (4) within airway (2) of the patient. While balloon (18) expands against the resilient bias provided by resilient tube (50), resilient tube (50) does not significantly increase the fluid pressure required to inflate balloon (18).

Figure 5C:
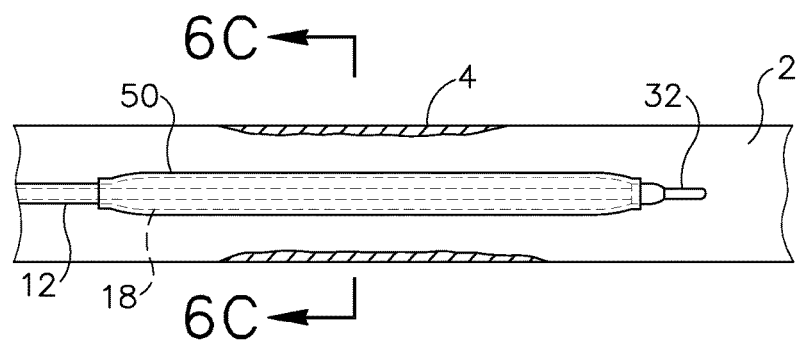
FIG. 5C depicts a detailed side elevation view of the inflatable balloon of FIG. 5A, deflated within a now dilated region of the airway.
Figure 6C:
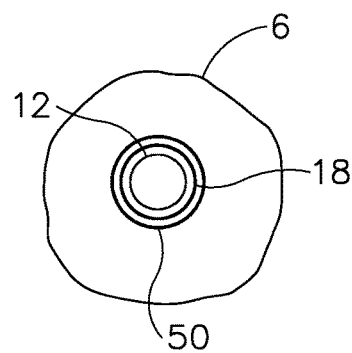
FIG. 6C depicts a cross sectional view of the inflatable balloon of FIG. 5A, taken along line 6C-6C of FIG. 5C.

Inflatable balloon (18) is then deflated, as shown in FIGS. 5C and 6C, leaving behind a now dilated region (6) within airway (2) of the patient. By way of example only, balloon (18) may be deflated by actively drawing the fluid from balloon (18); by venting the fluid in balloon (18), allowing the inward pressure imposed by airway (2) to drive fluid from balloon (18); or in any other suitable fashion as will be apparent to those of ordinary skill in the art in view of the teachings herein. As inflatable balloon (18) is deflated, resilient tube (50) continues to impose an inwardly directed resilient bias on the exterior of inflatable balloon (18), which drives the exterior of inflatable balloon (18) inwardly back toward its initial shape, as shown in FIGS. 5C and 6C.

It should be understood from the foregoing that resilient tube (50) assists in providing a reduced effective outer diameter or profile for deflated inflatable balloon (18), which may in turn facilitate insertion/retraction of deflated balloon (18) through airway (2). In addition to reducing the effective outer diameter for deflated inflatable balloon (18), resilient tube (50) may also provide an outer diameter that is substantially smooth and consistent along the length of balloon (18) and tube (50), which may also facilitate insertion/retraction of balloon (18) through airway (2). By way of example only, the pulling forces required to extract a balloon (18) with resilient tube (50) versus a balloon (18) without resilient tube (50) may be consistent with the merely illustrative prophetic values provided below:

TABLE 1

| Passageway Inner Diameter | 8.5 mm | 8 mm | 7.5 mm |
| --- | --- | --- | --- |
| Retraction Force for Balloon (18) with Resilient Tube (50) | 1.5 lbs. | 3.2 lbs. | 5.7 lbs. |
| Retraction Force for Balloon (18) without Resilient Tube (50) | 3.2 lbs. | 5.6 lbs. | 7.7 lbs. |

Furthermore, resilient tube (50) may substantially speed up the balloon (18) deflation process by helping to drive fluid out of balloon (18) due to the inwardly directed resilient bias imposed by tube (50). Resilient tube (50) may also provide an increased puncture resistance and burst resistance for balloon (18). Still other potential results from including resilient tube (50) will be apparent to those of ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A dilation device comprising:
(a) an elongate shaft;
(b) an inflatable balloon disposed along the shaft, wherein the inflatable balloon is configured to transition between a non-inflated configuration and an inflated configuration; and
(c) a resilient tube disposed along the shaft, wherein the resilient tube includes opposing proximal and distal ends, wherein the resilient tube partially encompasses the inflatable balloon such that the distal end of the resilient tube is positioned proximal to a distal end of the inflatable balloon, wherein the proximal end of the resilient tube is bonded to the shaft and the distal end of the resilient tube is longitudinally slidable relative to the distal end of the inflatable balloon while the proximal end remains bonded to the shaft, wherein the resilient tube is configured to expand and contract with the inflatable balloon as the inflatable balloon transitions between the non-inflated configuration and the inflated configuration, and wherein the resilient tube is configured to impose a resilient bias on at least a portion of an exterior of the inflatable balloon to thereby resiliently urge the inflatable balloon toward the non-inflated configuration, wherein at least part of the resilient tube is secured to one or both of the elongate shaft or the inflatable balloon.

2. The dilation device of claim 1, wherein the resilient tube is attached to the shaft near the proximal end of the inflatable balloon.

3. The dilation device of claim 1, wherein an interior of the resilient tube is at least partially adhered to the exterior of the inflatable balloon.

4. The dilation device of claim 1, wherein the shaft, the balloon, and the resilient tube together are configured to fit in an anatomical passageway in a patient.

5. The dilation device of claim 1, wherein the resilient tube comprises silicone.

6. The dilation device of claim 1, wherein the shaft defines a lumen, wherein the inflatable balloon is in fluid communication with the lumen.

7. The dilation device of claim 1, wherein the shaft further comprises a distal end and a proximal end, and wherein the inflatable balloon is disposed along the shaft at the distal end of the shaft.

8. The dilation device of claim 1, wherein the shaft contains at least one bend.

9. The dilation device of claim 1, wherein the shaft is flexible along at least a portion of a length of the shaft.

10. The dilation device of claim 9, wherein the inflatable balloon is disposed along the flexible portion of the shaft.

11. The dilation device of claim 1, wherein the proximal end of the resilient tube is permanently bonded to both the shaft and a proximal end of the inflatable balloon.

12. A dilation device comprising:
(a) an elongate shaft, wherein the shaft defines a lumen;
(b) an inflatable balloon disposed along the shaft, wherein the inflatable balloon is in fluid communication with the lumen; and
(c) a resilient tube disposed along the shaft, wherein at least a proximal end of the resilient tube is longitudinally fixed directly to the shaft at a location proximal to the inflatable balloon and at least a distal end of the resilient tube is longitudinally slidable along the shaft such that the distal end is not longitudinally fixed to the shaft or to the inflatable balloon, wherein the resilient tube is positioned to only partially encompass the inflatable balloon.

13. The dilation device of claim 12, wherein the inflatable balloon is inflatable to a size configured to dilate an airway in a patient.

14. The dilation device of claim 12, wherein the resilient tube is operable to drive fluid from the inflatable balloon.

15. The dilation device of claim 12, wherein the resilient tube has a length of approximately 3 inches.

16. The dilation device of claim 12, wherein the resilient tube has an inner diameter between approximately 0.125 inches and approximately 0.135 inches.

17. The dilation device of claim 12, wherein the resilient tube has a wall thickness between approximately 0.025 inches and approximately 0.030 inches.

18. The dilation device of claim 12, wherein the dilation device further comprises a stylet, wherein the stylet is configured to be received through the lumen, wherein the stylet comprises a core member with a proximal end and a distal end, and wherein a coil is disposed around at least part of the distal section of core member.

19. A dilation device comprising:
   (a) a flexible elongate shaft, wherein the shaft defines a lumen, wherein the flexible elongate shaft includes at least one bend;
   (b) an inflatable balloon disposed along and bonded to the shaft, wherein the inflatable balloon is in fluid communication with the lumen; and
   (c) a resilient tube including opposing proximal and distal ends, wherein the proximal end of the resilient tube is bonded to both the shaft and a proximal end of the inflatable balloon, wherein the distal end is configured to longitudinally translate in a proximal direction relative to a distal end of the inflatable balloon while the proximal end remains bonded to the shaft, wherein the resilient tube encompasses at least a portion of the inflatable balloon, wherein the resilient tube is configured to impose an inwardly directed resilient bias on an exterior of the inflatable balloon.

20. The dilation device of claim 19, wherein the dilation device further comprises a stylet, wherein the stylet is configured to be received through the lumen, wherein the stylet comprises a core member with a proximal end and a distal end, and wherein a coil is disposed around at least part of the distal section of core member.

\* \* \* \* \*